(12) United States Patent
Metcalf

(10) Patent No.: US 7,452,715 B1
(45) Date of Patent: Nov. 18, 2008

(54) PRODUCTION OF THE LIPIDATED FORM OF THE PEPTIDOGLYCAN ASSOCIATED LIPOPROTEINS OF GRAM-NEGATIVE BACTERIA

(75) Inventor: Benjamin J. Metcalf, Rochester, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/019,164

(22) PCT Filed: Jun. 20, 2000

(86) PCT No.: PCT/US00/17020

§ 371 (c)(1),
(2), (4) Date: Dec. 20, 2001

(87) PCT Pub. No.: WO01/00790

PCT Pub. Date: Jan. 4, 2001

Related U.S. Application Data

(60) Provisional application No. 60/141,061, filed on Jun. 25, 1999.

(51) Int. Cl.
*C12N 15/00* (2006.01)
*C12N 1/20* (2006.01)

(52) U.S. Cl. ................... 435/320.1; 435/252.3

(58) Field of Classification Search .............. 435/320.1, 435/243, 252.3
See application file for complete search history.

(56) References Cited

FOREIGN PATENT DOCUMENTS

WO        WO/90 02557 A     3/1990

OTHER PUBLICATIONS

Baneyx (Current Opinion in Biotechnology, 10:411-421, 1999).*
Makrides et al (Microbiological Reveiws, 60(3):512-538, Sep. 1996).*
Green, B.A., et al., *Infect Immun.*, 59, (3191-3198), (1991).
Green, B.A., et al., *Infect. Immun.*, 58, (3272-3278), (1990).
Zlotnick, G.W., et al., *J. Biol. Chem.*, 263, (9790-9794 ), (1988).
Lim, A., Jr., et al., *Microbiology*, 143, (1709-1716), (1997).
Guzman, L.M., et al., *J. Bacteriol.*, 177, (4121-4130), (1995).
Mertens, N., et al., *Gene*, 16, (9-15), (1995).
Mertens, N., et al., *Biotechnology* (N.Y.), 13 (175-179), (1995).
Chandrashekharan, S., et al., *Biol. Chem.*, 379, (579-582), (1998).
Reddy, P. et al., *Nucleic Acids Res.*, 25, (10473-10488), (1989).
Sagawa, H., et al., *Gene*, 168, (37-41), (1996).
Waleh, N. S. *Gene*, 117, (7-14), (1992).
Skerra, A., *Gene*, 151, (131-5), (1994).
Haldimann, A., et al., *J. Bacteriol.*, 180, (1277-1286), (1998).
Lutz, R., et al., *Nucleic Acids Res.*, 25, (1203-1210), (1997).
Wulfing, C., *Gene*, 136, (199-203), (1993).
Nelson, M. B., et al., "Cloning and sequencing of *Haemophilus influenzae* outer membrane protein P6". *Infection and Immunity*, vol. 56, No. 1, Jan. 1988, pp. 128-134.
Yang, Y.P. et al: Effect of lipid modification on the physicochemical, structural, antigenic and immunoprotective properties of *Haemophilus influenzae* outer membrane protein P6: *Vaccine GB, Butterworth Scientific Guildford*, vol. 15, No. 9, Jun. 1, 1997, pp. 976-987.

* cited by examiner

*Primary Examiner*—Patricia A Duffy
(74) *Attorney, Agent, or Firm*—Joel B. Silver; Alan Gordon; Michael Moran

(57) ABSTRACT

The expression of the lipidated form of the peptidoglycan-associated protein (PAL) of gram-negative bacteria is achieved through the use of a plasmid containing a tightly regulated promoter. A bacterial host cell is transformed, transduced or transfected with such a plasmid. The host cell is then cultured under conditions such that the lipidated recombinant PAL is expressed. The lipidated recombinant PAL is included in an antigenic composition administered to a mammalian host to immunize against a gram-negative bacterium.

8 Claims, 3 Drawing Sheets

SEQUENCE LISTING

<160> NUMBER OF SEQ ID NOS: 2

<210> SEQ ID NO 1

```
<211> LENGTH: 24
<212> TYPE: DNA
<213> ORGANISM: Haemophilus influenzae

<400> SEQUENCE: 1
ggagaaatca tatgaacaaa tttg                                             24

<210> SEQ ID NO 2
<211> LENGTH: 32
<212> TYPE: DNA
<213> ORGANISM: Haemophilus influenzae

<400> SEQUENCE: 2
ggatcctgtt tttcaagctt agaaatacta ag                                    32
```

PRODUCTION OF THE LIPIDATED FORM OF THE PEPTIDOGLYCAN ASSOCIATED LIPOPROTEINS OF GRAM-NEGATIVE BACTERIA

CROSS-REFERENCE TO RELATED APPLICATIONS

The present application is a 371 of PCT/US00/17020 filed on Jun. 20, 2000 and claims the benefit of U.S. provisional application No. 60/141,061 filed on Jun. 25, 1999.

FIELD OF THE INVENTION

This invention is directed to the expression of the lipidated form of the peptidoglycan-associated protein of gram-negative bacteria and the use of that recombinant lipidated protein in antigenic compositions.

BACKGROUND OF THE INVENTION

The cell walls of gram-negative bacteria contain cross-linked moieties known as peptidoglycans. A number of gram-negative bacteria produce proteins which are covalently linked to the peptidoglycans. Such a protein is referred to as a peptidoglycan-associated lipoprotein (PAL). PALs are present as part of the tol locus in a number of gram-negative bacteria, including Legionella pneumophila (Bibliography entry 1), Escherichia coli (2), Haemophilus ducreyi (3), Campylobacter jejuni (4), Pseudomonas putida (5), Brucella abortus (6), Pseudomonas aeruginosa, Klebsiella aerogenes, Serratia marcescens, Proteus vulgaris, Salmonella typhimurium (7) Actinobacillus pleuropneumoniae (8), Helicobacter pylori (9) Chlamydia pneumoniae (10), and Chlamydia trachomatis (11).

Other PAL-containing bacteria are the Haemophilus influenzae (H. influenzae) bacteria. The H. influenzae bacteria are divided into two groups. Those strains which possess a known capsule are typed by the serological reaction of the capsule with reference antisera. Types a-f have been identified. Strains which fail to react with any of the reference antisera are known as nontypable.

H. influenzae type b (Hib) is the most frequent cause of neonatal meningitis and other invasive infections in the United States (12). The major incidence of childhood meningitis occurs between the ages of one and five years. Sixty percent of those meningitis cases due to Hib occur in children under the age of two (12).

Nontypable H. influenzae (NTHi) is a gram-negative organism which causes a number of diseases, including pneumonia, bacteremia, meningitis, postpartum sepsis, and acute febrile tracheobronchitis in adults (13). NTHi has been reported to cause between 20 and 40 percent of all cases of otitis media seen in young children (14, 15, 16). Children may experience multiple infections due to the same organism since infection confers no long lasting immunity. Current therapy for chronic or repeated occurrences of otitis media includes administration of antibiotics and insertion of tubes to drain the inner ear. NTHi strains have also been implicated as a primary cause of sinusitis (17). Additionally, NTHi causes neonatal sepsis.

Current capsular-based antigenic compositions are ineffective against NTRi. The surface of these bacteria has been shown to be extremely antigenically variable, with the major outer membrane proteins, P1 and P2, being particularly diverse (18, 19). In humans, the presence of serum bactericidal antibodies has been reported to correlate with protection from otitis media caused by sensitive NTHi strains (20).

Candidates for inclusion in antigenic compositions against NTHi should be highly conserved at the amino acid level, surface exposed (in particular, outer membrane proteins), elicit bactericidal antibodies, and be present in all isolates. Previous research has shown that the P6 (also known as PBOMP-1 and HiPAL) (21) protein of NTHi meets all of these criteria. The purified native proteins have been shown to elicit bactericidal antibodies (22, 23, 24, 25) and are conserved antigenically (22, 23, 26, 27).

Evaluation of the genetic sequence of the P6 gene has shown that it is highly conserved among otic NTHi isolates and thus the protein sequence is also highly conserved. Native P6 is a lipoprotein, more specifically a PAL, which is modified at the amino-terminal cysteine with lipids. This protein is present in H. influenzae in relatively small amounts (less than 1% of total outer membrane proteins), making purification from the native organism of useful quantities quite difficult. Thus, a recombinant version of P6 is required for further development as a component in antigenic compositions.

Several laboratories were unable to express lipidated rP6 in large quantities in E. coli (28, 29). As a result, initial recombinant constructs expressing P6 in E. coli could express only a nonlipidated version of the protein. These groups reported that, while the lipidated P6 protein purified from H. influenzae was more immunogenic than nonlipidated rP6 purified from E. coli, it was difficult to engineer a DNA vector which would express lipidated P6 (28, 29); i.e., not better than the low levels of native P6 expressed by H. influenzae.

Previous attempts to express lipidated rP6 relied on promoters which were not under tight transcriptional regulation, such as trc, taq, lac and $P_L$-C1857. It was theorized that this somewhat leaky transcription led to subtle effects on the E. coli which contributed to low levels of expression of the lipidated protein. Experimental evidence indicated that the ability of signal peptidase II to add lipid to the N-terminus of the protein was not responsible for the low yield of processed P6 (data not shown).

While the P6 protein of H. influenzae has been a primary candidate for inclusion in antigenic compositions against Haemophilus disease (20, 23, 24, 25, 30, 31), the relatively small amounts available from H. influenzae have made recombinant expression of this protein essential. Previous efforts to express lipidated P6 protein in meaningful quantities have been unsuccessful (28, 29). Thus, researchers have focused on the expression and purification of multiple forms of nonlipidated P6.

The antibody response engendered by the nonlipidated rP6 was biologically functional, capable of protecting infant rats from meningitis (28) and eliciting bactericidal antibodies (28, 29), but of a lower magnitude than those elicited by lipidated native P6 (28).

Therefore, there is a need to construct host cell-expression vector systems which express lipidated PALs of gram-negative bacteria. In particular, there is a need to construct host-cell expression vector systems which express lipidated rP6, which can then be included in antigenic compositions against H. influenzae.

SUMMARY OF THE INVENTION

Thus, it is an object of this invention to develop genetic constructs capable of expressing lipidated PALs of gram-negative bacteria in bacterial host cells.

It is a particular object of this invention to develop genetic constructs capable of expressing lipidated rP6 in bacterial host cells, in particular, in *E. coli*.

It is a further object of this invention to include that lipidated rP6 in antigenic compositions for administration to a mammal to prevent disease caused by *H. influenzae*.

These and other objects of the invention as discussed below are achieved by the cloning and expression in bacterial cells of the lipidated forms of PALs through the use of tightly regulated promoters in the expression vectors.

The invention is exemplified by the cloning and expression in bacterial cells of the lipidated form of recombinant *H. influenzae* P6 protein through the use of such promoters in the expression vector.

Specifically, for the expression of lipidated recombinant P6, plasmids are constructed which contain an arabinose inducible promoter or a T7 promoter, wherein the promoter is operatively linked to an isolated and purified DNA sequence comprising a DNA sequence which encodes the P6 protein, and wherein the DNA sequence, under the control of said promoter, is expressed in lipidated form.

In turn, a bacterial host cell is transformed, transduced or transfected with such a plasmid and is then cultured under conditions which permit the expression of the lipidated rP6 by the host cell.

In another embodiment of this invention, the lipidated rP6 is used as an immunogen in antigenic compositions against all pathogenic *H. influenzae*, including both type b and nontypable *H. influenzae*.

When purified, the recombinant protein is indicated to be lipidated by several criteria and, most importantly, is much more immunogenic than the non-lipidated form of P6 previously used.

The lipid modification of the amino-terminal cysteine by signal peptidase II has been shown to make proteins more immunogenic than their non-lipidated forms (28, 29, 32). These forms have been evaluated for immunogenicity and antigenic relatedness to lipidated P6. All have shown decreased immunogenicity as compared to the native lipidated protein.

This allows much lower doses to be used to immunize humans and thus makes the lipidated rP6 a more commercially viable candidate for inclusion in antigenic compositions. These increased titers allow the use of lower P6 protein doses in humans, which would provide a cost savings in the production of that protein.

The isolated and purified lipidated rP6 protein is used to prepare an antigenic composition which elicits a protective immune response in a mammalian host. The antigenic composition may further comprise one or more of an adjuvant, diluent or carrier. Examples of such adjuvants include aluminum hydroxide, aluminum phosphate, Stimulon™ QS-21, MPL™, IL-12 and cholera toxin. The antigenic composition is administered to a mammalian host in an immunogenic amount sufficient to protect the host against disease caused by *H. influenzae*.

BRIEF DESCRIPTION OF THE FIGURES

FIG. 2 depicts the homogeneity and identity of lipidated rP6. Fifteen percent SDS-PAGE gels were loaded with samples containing approximately 10 μg of lipidated rP6 in the initial extract (lane 1) and the pool of anion exchange purified lipidated rP6 (lane 2). Lanes labeled S contain prestained low molecular weight standards from Bio-Rad.

DETAILED DESCRIPTION OF THE INVENTION

Figure 1:
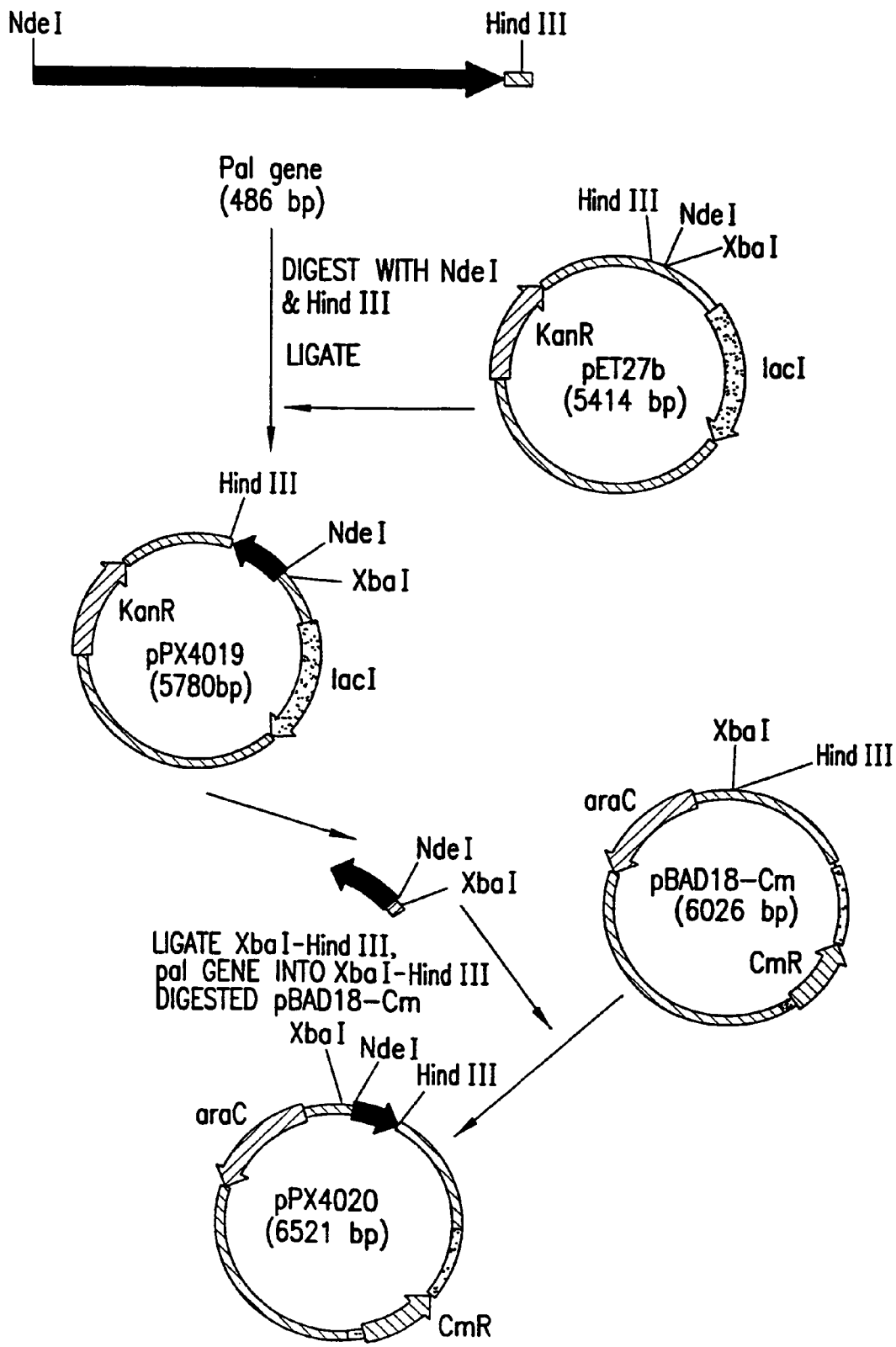
FIG. 1 depicts the cloning of the pal gene encoding the P6 protein with the native lipoprotein signal peptide by PCR amplification from the chromosome of nontypable *H. influenzae* strain P860295.

In order to overcome the recognized difficulty in expressing usable amounts of lipidated PALs, such as lipidated rP6, a strategy was devised involving the use of tightly regulated promoters and host strains devoid of cytoplasmic and perplasmic proteases.

Previous unsuccessful efforts to express lipidated P6 protein in meaningful quantities for commercial use all relied on changing the promoter sequence and/or making changes in the signal sequence recognized by signal peptidase II.

As discussed below, plasmids were constructed containing the pal gene encoding P6 under the control of the T7 promoter (plasmid pPX4019—Example 1) and the arabinose inducible promoter (plasmid pPX4020—Example 2). Exemplary bacterial strains and media are described in Example 3. Both pPX4019 and pPX4020 express lipidated P6 protein in the *E. coli* strains tested, as determined by western blot analysis with P6-specific monoclonal antibodies, sizing on SDS-PAGE gels which indicated a lack of a signal sequence and visual observation of expression levels in Coomassie stained gels (see Example 4 and Figures).

Plasmid pPX4020 produced increased levels of rP6 protein expression in the *E. coli* strains BL21 and BLR, with the highest levels in strain BLR. Therefore, plasmid pPX4020 was chosen for further studies. Growth of larger quantities of lipidated rP6 expressing *E. coli* was performed in host strain BLR. All subsequent experiments utilized this host-vector system.

The plasmid construct described herein as a preferred embodiment (pPX4020) uses the arabinose inducible promoter system which has several unique features: It is tightly regulated and almost completely inactive if no arabinose is present and some glucose is present. It is also modulatable in that it shows increasing induction levels as increasing arabinose is added to the culture medium. These factors in combination with the BLR strain of *E. coli*, which is highly protease deficient and recombination deficient, allow significant expression of the lipidated P6 protein.

Batch scale purification of lipidated rP6 involves differential centrifugation, differential detergent extraction and anion exchange chromatography (see Example 4).

However, to become a viable candidate for inclusion in an antigenic composition, the expressed lipidated rP6 must be purified by a method which is amenable to large scale. Diafiltration is a method suitable to large scale purification. The diafiltration process for extracting lipidated rP6 is complicated because lipidated rP6 is tightly associated with peptidoglycans.

As described in Example 5, solubilization of the lipidated rP6 was accomplished following differential detergent extraction much like the native protein obtained from *Haemophilus* (Hi-P6) (33), but with tangential flow diafiltration used instead of centrifugation. Detergents such as dodecylmaltoside, deoxycholate, Zwittergent™ 3-08, 3-12, and 3-14 were all tested and found to be acceptable to extract the lipidated rP6 when used in the 0.2-1% (w/v) range. The lipidated rP6 could also be solubilized in a sodium borate buffer, pH 9.5 at 65° C. The flexibility of detergent choice permitted the use of Zwittergent™ 3-12 to extract the lipidated rP6. The choice of Zwittergent™ 3-12 thus minimizes the number of components required to produce a multi-component antigenic composition. Whereas the native Hi P6 is obtained in essentially pure form following solubilization, the recombinant protein is solubilized along with several *E. coli* proteins. The relative amount of these proteins can be varied and in some cases nearly eliminated by the choice of detergent used in the final extract. The lipidated rP6 is separated from any remaining *E. coli* proteins by anion exchange chromatography (see Example 6).

This method of extracting PALs combines the clarification and extraction processes into one unit operation. The product is extracted from the cells and it is separated from cell debris with only one continuous diafiltration process. In addition, the PALs are extracted in a semi-purified state which simplifies the downstream processing steps. Finally, this process is very scalable, because the only requirement is that the surface area of the membranes be increased proportionally with the amount of cells. This extraction process avoids the use of centrifugation, a method which is not preferred for use in large scale extraction. After extraction, the lipidated rP6 is purified by conventional techniques.

Analysis of the lipidated rP6 was consistent with the characterization of the recombinant protein as a lipoprotein, as expected. The molecular size as determined by MALDI-TOF mass spectrometry shows that the purified recombinant protein is larger than expected from its amino acid sequence alone (see Example 7). The size of the protein, combined with the amino acid analysis detailed in Table 1 (see Example 8), indicate that the signal sequence has been removed and the protein is in the mature form. The existence of a blocked amino-terminus, as demonstrated by amino-terminal amino acid analysis (see Example 9), also shows that modification of the terminal cysteine residue has taken place. Taken together, these results show that the signal sequence, which has been shown to be recognized and processed by *E. coli* resulting in lipidated P6 (23), has been removed and that the recombinant P6 purified here is lipidated at its amino-terminus.

Previous investigators have demonstrated that antibody levels against P6 after naturally occurring NTHi infections have an inverse correlation with disease incidence (34, 35, 36), making the production of high titers against P6 a goal of any immunization program using this antigen. The native lipidated P6 protein is present in very small quantities (less than 1% of the outer membrane proteins) (33), which makes purification of commercially viable quantities problematic at best.

A critical advantage of the lipid-modified rP6 over the previously expressed non-lipidated rP6 is the enhanced immunogenicity associated with the lipid modification. Two reports have shown that, while non-lipidated rP6 is capable of eliciting biologically active antibodies, it is less immunogenic than the native lipidated protein (28, 29).

In contrast, the animal immunogenicity data presented in Tables 2-4 below (see Examples 10 and 11) show that the lipid modification of recombinant P6 also increases the immunogenicity of this antigen in the mouse model. The up to a 2-log increase in geometric mean antibody titers (GMT) at week 6 is quite significant and makes the lipidated form of the rP6 protein a practical candidate for inclusion in antigenic compositions. This is bolstered by the results in these experiments that lipidated rP6 did not interfere with the immune response generated by the other antigens tested.

Taken together, these data support the view that lipidated rP6 is viable for inclusion in antigenic compositions against *H. influenzae*. Although exemplified below with lipidated rP6 from NTHi, lipidated rP6 from Hib is also suitable for inclusion in the antigenic compositions of this invention.

A variety of bacterial host cell-vector systems are suitable for use to express the lipidated rP6 protein used in the antigenic compositions of this invention in addition to those detailed in Examples 1-3.

These expression systems place the gene encoding the recombinant lipidated PAL under the control of a tightly regulated promoter. Under specific conditions, these promoters operate to down regulate the production of the recombinant PAL mRNA, and consequently mitigate any detrimental effects on the host cell due to the production of the recombinant lipidated PAL (37). This tight regulation can then be removed under specific conditions to allow for maximized recombinant lipidated PAL expression in the host cell.

These tightly regulated promoters (which may be together with other control elements) include, but are not limited to, the arabinose inducible promoter (38), the T7 promoter which may be modified to be under control by nutL/N antitermination function (39, 40) or by Mu C (41), the $P_L$ promoter in combination with antiterminator (42), the SP6 RNA polymerase and SP6 promoters (43), the colicin promoter (44), the tetA promoter/operator (45), the rhamnose and phosphate promoters (46), the LacR/O, tetR/O and AraCI1-12 regulatory elements (47), and invertible promoters (48).

The vector system is compatible with the host cell used. Suitable host cells include bacteria transformed, transfected or transduced by conventional techniques with plasmid DNA, cosmid DNA or bacteriophage DNA. Examples of bacterial hosts include *E. coli, B. subtilis, Salmonella* and *Shigella*.

To construct such a vector, the pal DNA is inserted into a plasmid vector containing a promoter under tight transcriptional control, and other control elements are ligated into specific sites within the vector, so that when the plasmid vector is inserted into a bacterial host cell, the pal DNA can be expressed by the host cell.

The plasmid is introduced into the host cell by transformation, transduction or transfection, depending on the host cell-vector system used. The host cell is then cultured under conditions which permit expression of the lipidated rP6 protein by the host cell. A host cell containing a plasmid with the arabinose inducible promoter is induced with L-arabinose, while a host cell containing a plasmid with the T7 promoter is induced with IPTG.

The lipidated PALs are useful in the preparation of antigenic compositions to confer protection to mammals against diseases caused by the corresponding bacteria. For example, the lipidated rP6 protein is useful in the preparation of antigenic compositions to confer protection to mammals against diseases caused by *H. influenzae*.

These antigenic compositions comprise an isolated and purified lipidated PALs, such as lipidated rP6 protein, wherein the antigenic composition elicits a protective immune response in a mammalian host. Multivalent antigenic compositions are provided by including other proteins, such as by combining the lipidated rP6 with the UspA2 protein of *Moraxella catarrhalis* (which is described in PCT International Application Number WO 98/28333 (49), which is hereby incorporated by reference), a causative agent of bacterial otitis media, and the recombinant lipidated rP4 protein of *H. influenzae* (also known as protein "e") (which is described in U.S. Pat. No. 5,601,831 (50), which is hereby incorporated by reference).

Antigenic compositions containing a lipidated PAL, such as lipidated rP6 protein, may be mixed with immunologically acceptable diluents or carriers in a conventional manner to prepare injectable liquid solutions or suspensions. Such diluents or carriers include, but are not limited to, PBS, physiologic saline, buffered isotonic solutions, liposomes and ISCOMS. The level of antibodies elicited by the antigenic compositions may be improved by using certain adjuvants such as aluminum hydroxide, aluminum phosphate, Stimulon™ QS-21 (Aquila Biopharmaceuticals, Inc., Framingham, Mass.), MPL™ (3-O-deacylated monophosphoryl lipid A; RIBI ImmunoChem Research, Inc., Hamilton, Mont.), IL-12 (Genetics Institute, Cambridge, Mass.), the heat-labile toxin of *E. coli*, and cholera toxin (either in a wild-type or mutant form, for example wherein the glutamic acid at amino acid position 29 is replaced by another amino acid, preferably a histidine, in accordance with PCT International Application Number WO 00/18434) (51).

The antigenic compositions of this invention are administered by injection in a conventional manner, such as subcutaneous, intradermal or intramuscular injection into humans, as well as by oral, mucosal, intranasal or vaginal administration, to induce an active immune response for protection against disease caused by a gram-negative bacterium, such as *H. influenzae*. The dosage to be administered is determined by means known to those skilled in the art. Protection may be conferred by a single dose of the antigenic compositions, or may require the administration of several doses, in addition to booster doses at later times to maintain protection.

In order that this invention may be better understood, the following examples are set forth. The examples are for the purpose of illustration only and are not to be construed as limiting the scope of the invention.

EXAMPLES

Standard molecular biology techniques are utilized according to the protocols described in Sambrook et al. (52).

Example 1

Construction of Plasmid pPX4019 Containing the pal Gene and the T7 Promoter

As depicted in FIG. 1, the pal gene encoding the P6 protein was cloned with the native lipoprotein signal peptide by PCR amplification from the chromosome of non-typable *H. influenzae* strain P860295. Using mutagenic primers which created an NdeI restriction site encompassing the start codon at the 5' end of the gene (GGAGAAAT CATATGAACAAATTTG) (SEQ ID NO:1) and a HindIII site in the region 3' of the stop codon (GGATCCTGTTTTTC AAGCTTAGAAATACTAAG) (SEQ ID NO:2), the PCR fragment containing the pal gene was cloned into the pCRII expression vector (Invitrogen, Carlsbad, Calif.) and screened by restriction analysis. The resulting plasmid was used as the source for the NdeI/HindIII fragment containing the pal gene for P6 which was cloned into the NdeI and HindIII sites of expression vector pET27b (Novagen, Madison, Wis.). The design of this construction places the gene for P6 under the control of the T7 promoter and takes advantage of a consensus ribosome binding site in the vector. The initial clones were identified in a non-permissive *E. coli* host (DH5α) by restriction analysis. A single plasmid isolate was chosen and saved as pPX4019. This plasmid was used to transform the permissive host strain BL21(DE3,pLysS) (Novagen) for expression studies.

Example 2

Construction of Plasmid pPX4020 Containing the Pal Gene and the Arabinose Inducible Promoter A second P6 protein expression plasmid was constructed placing the pal gene under the control of the tightly regulated arabinose inducible promoter (38). This plasmid was generated by subcloning the XbaI/HindIII fragment from the plasmid pPX4019 containing the pal gene and the consensus ribosome binding site from pET27b into the similarly digested plasmid pBAD18-Cm (see FIG. 1). Clones were screened by restriction analysis followed by expression studies on selected candidates. One of the pBAD18-Cm isolates which expressed P6 protein was designated pPX4020.

Example 3

Expression of Lipidated rP6 from pPX4019 and pPX4020

Qualitative expression studies comparing different isolates, plasmid constructs, *E. coli* host strains and concentration of inducer (IPTG for pPX4019, L-arabinose (Sigma Chemical Co., St. Louis, Mo.) for pPX4020) were all performed in a similar manner to provide for a consistent background for comparison. Single colony isolates were grown overnight at 37° C. in HySoy™ media, 1% glucose and the appropriate antibiotic for plasmid selection (pPX4019, 15 µg/ml Kanamycin; and pPX4020, 15 µg/ml Chloramphenicol). These cultures were diluted to a $OD_{600}$=0.5 in HySoy™ 1% glycerol and antibiotic, grown at 37° C. to a $OD_{600}$=2-4 and induced. Samples equivalent to a $OD_{600}$=1.0 were taken at time points just prior to induction, at two hours and 18 hours post-induction. These samples were centrifuged and the cell pellets resuspended in 150 µl SDS-PAGE loading buffer (ISS, Natick, Mass.). Comparisons were made from Coomassie blue stained 15% SDS-PAGE gels with 15 µl of sample loaded per lane.

*E. coli* Host Cell Strains Used to Express Lipidated rP6 from Plasmid pPX4019:

DH5α—φ80dlacZΔM15 Δ(lacZYA-argF)U169 deoR recA1 endA1 hsdR17 ($r_k^-$,$m_k^+$) phoA supE44λ⁻ thi-1 gyrA96 relA1 (Life Technologies, Rockville, Md.)

BL21(DE3)—ompT lon $hsdS_B$ ($r_B^-$ $m_B^-$) gal dcm (DE3) (Novagen)

*E. coli* Host Cell Strains Used to Express Lipidated rP6 from Plasmid pPX4020:

DH5α—φ80dlacZΔM15 Δ(lacZYA-argF)U169 deoR recA1endA1 hsdR17 ($r_k^-$,$m_k^+$) phoA supE44λ⁻ thi-1 gyrA96 realA1 (Life Technologies)

BLR—ompT lon $hsdS_B$ ($r_B^-$ $m_B^-$) gal dcm Δ(srl-recA) 306::Tn10 (tet$^r$) (Novagen)

BL21 (DE3)—ompT lon hsdS$_B$ (r$_B^-$ m$_B^-$) gal dcm (DE3) (Novagen)

Growth of *E. coli* BLR(pPX4020) Expressing L-rP6:

Recombinant *E. coli* cells expressing lipidated rP6 were grown in a fermenter as described below. Growth media containing the following materials was prepared and sterilized in situ for fermenters and by autoclaving for flask growth.

Solution A.

| Material | g/L* |
|---|---|
| Potassium phosphate, monobasic | 3.0 |
| Potassium phosphate, dibasic | 7.0 |
| Ammonium sulfate | 1.0 |
| Sodium citrate dihydrate | 1.0 |
| Ferrous sulfate, heptahydrate | 0.09 |
| Glycerol (Remove flask medium before adding) | 5 mL/L |
| Sodium Sulfate | 0.58 |
| 1000X Trace Mineral Solution (see below) | 1 mL/L |
| Do not pH adjust - Autoclave | |

*unless otherwise stated

| 1000X Trace Mineral Solution | g/100 mL |
|---|---|
| Zinc sulfate, heptahydrate | 3.0 |
| Cupric sulfate, pentahydrate | 0.9 |
| Manganese sulfate, monohydrate | 0.42 |
| Cobalt chloride, hexahydrate | 0.06 |
| Molybdic acid | 0.15 |

Pre-Inoculation Feed Solution: MCG

| Ingredient | g/L |
|---|---|
| Glucose | 500 |
| Magnesium sulfate, heptahydrate | 11 |
| Calcium chloride | 0.83 |

EDTA Solution

| Ingredient | g/L |
|---|---|
| EDTA | 186.15 |

Sterile media containing Solution A and the Mineral solution was aliquoted into shake flasks and 20 ml of MCG added per liter of media. Chloramphenicol was added to 50 μg/ml. The starter cultures were inoculated with 200-300 l of *E. coli* BLR (pPX4020) from a frozen stock. The cells were grown at 30° C. with aeration for 16 hours. A 10 liter fermenter containing growth media, supplemented as above, was inoculated with the above culture to an OD$_{600}$ of approximately 0.2.

Fermenter control parameters were set as follows:

| Temperature | 36° C. |
|---|---|
| pH = | 7.0 +/− 0.1 |
| D.O. = | 20 to 50% by agitation and pure oxygen |
| Air and oxygen flow = | 20% on rotameter |
| Antifoam | one drop if necessary |
| Backpressure | 0.5 bar |

The following solutions were used for control of run parameters and were sterilized prior to use: PPG-2000-200 mL for foam control if necessary, 40% ammonium hydroxide—1 L for pH control during growth, 50% glucose—1 L to feed when pH began to rise due to glucose depletion—for continued growth, 4 N acetic acid—500 mL for pH control during induction, 25% arabinose solution, (250 g/L) sterile filtered+1% glycerol—250 mL (pre-autoclaved). The arabinose/glycerol solution was used to feed after final glucose addition when pH began to rise due to glucose depletion to induce production of protein. The arabinose solution was filter sterilized prior to addition of the autoclaved glycerol stock. The solution was made by adding 100 mL glycerol and 400 mL of 25% arabinose solution for a 10 L fermentation. The final fermenter concentration contained 10 grams/liter arabinose and 10 ml/Liter glycerol.

After inoculation of the fermenter, base (sodium hydroxide) was added as needed for pH control, along with antifoam (PPG-2000) as needed. Pure oxygen was fed at 800 rpms. When the pH rose above 7.0, 900 mL of 50% glucose was fed to the culture. When the pH was greater than or equal to 7.1, an additional 200 mL of 50% glucose solution was added. These conditions were continued until an OD$_{600}$ of approximately 50 was reached.

After an OD$_{600}$ of approximately 50 was reached, when the pH rose above 7.0 again, 500 mL of arabinose/glycerol solution was added to induce expression of the LrP6. At this time, acid was used for further pH control. Incubation was continued for three hours post-induction, and then the culture was harvested following addition of 10 mL per liter of 500 mM EDTA solution, pH 8. The culture broth was stored at 4° C. until purification of the lipidated rP6.

Example 4

Batch Scale Analytical Purification of Lipidated rP6 by Differential Detergent Membrane Extraction Batches of the lipidated rP6 expressed from pPX4020 were utilized in subsequent experiments, and were purified by differential detergent membrane extraction as follows:

1) Isolation of the *E. coli* membrane fraction: Frozen bacterial cell pellets obtained from fermentation were thawed and suspended in 10 mM HEPES-NaOH, pH 7.4, 1 mM Na$_2$EDTA with a volume of buffer equal to five times the weight of the frozen cell pellet. The cell suspension was homogenized in a Microfluidics (Newton, Mass.) 110-Y microfluidizer to lyse the cells. The membranes were obtained from the cell lysate by differential centrifugation (300,000×g for 1 hour). The membranes were washed twice with the same volume of the buffer used for lysis, and then frozen as a pellet.

2) Solubilization of Lipidated rP6 from *E. coli* membranes: The lipidated P6 was solubilized from *E. coli* using differential detergent extraction similar to that described by Zlotnick et al (33) and Green et al (22). All extractions were carried out for 30 minutes at room temperature unless otherwise stated. All centrifugations were performed using a Beckman 45Ti rotor at 42,000 rpm for one hour with the temperature of the rotor controlled to 10° C. unless stated differently. *E. coli* membranes were suspended in 10 mM HEPES-NaOH, pH 7.4, 1 mM $MgCl_2$ and extracted twice with Triton™ X-100 (Calbiochem-Novabiochem International, San Diego, Calif.) at a final concentration of 1% (w/v) to remove inner membrane components. The resulting outer membrane pellet was suspended in 50 mM Tris™ HCl, pH 8, 5 mM $Na_2EDTA$, which was also used to suspend the subsequent pellets prior to the solubilization of the lipidated rP6. The outer membranes were then sequentially extracted two times with 1% Zwittergent™ 3-14; two times with 1% Zwittergent™ 3-14 and 0.5M NaCl; two times with 1% N-lauryl sarcosine, Na salt; 1% Zwittergent™ 3-14. The final pellet obtained after these extractions was extracted with 0.2% Zwittergent™ 3-12 in 10 mM Tris™ HCl, pH 8, 1 mM $Na_2EDTA$ for 45 minutes at 55° C. with intermittent mixing followed by centrifugation for at least one hour. The supernatant from this final extraction contained the lipidated rP6.

3) Purification of Lipidated rP6: The lipidated rP6-containing extract obtained as described above was further purified by anion exchange chromatography utilizing a DEAE fast flow resin (Amersham Pharmacia Biotech, Piscataway, N.J.) and the same low ionic strength buffer utilized for extraction. The solubilized lipidated rP6 was adsorbed to a DEAE fast flow column with a bed volume of approximately 20 mL. The column was developed with a 0-0.2M NaCl gradient over 40 minutes, followed by 20 minutes of an isocratic elution with 0.2M NaCl. The lipidated rP6 eluted during the isocratic phase of the development. Most of the other proteins remained adsorbed to the column and were later desorbed with 1M NaCl. Approximately 100 mg was purified from 200 g cells.

Figure 2A:
FIG. 2A is the Coomassie stained gel.
Figure 2B:
FIG. 2B is the western immunoblot of a similar gel.

4) Characterization of purified lipidated rP6 by SDS-PAGE and Western blot: The homogeneity of purified lipidated rP6 was assessed by SDS-PAGE in the Laemmli buffer system, followed by laser densitometry of the stained gel. Approximately 10 μg of LrP6 was analyzed from both the crude extract and anion exchange purified pool on a 15% SDS-PAGE gel (53). The gel was stained with Coomassie Blue and scanned in a laser densitometer. Laser densitometry of the Coomassie stained gel (FIG. 2A, lane 2) revealed a single peak of greater than 98% homogeneity in the pooled anion exchange fractions, indicating that lipidated rP6 had been purified to near homogeneity. The identity of lipidated rP6 in these samples was verified by reacting a western blot of the same samples used to determine homogeneity with monoclonal antibodies specific for the *Haemophilus influenzae* P6, which do not react to the related protein of *E. coli* (data not shown). Results of the western blot analysis are shown in FIG. 2B. The lipidated rP6 band was the only band reactive with the P6-specific monoclonal antibody in either the crude extract (lane 1) or the pooled fractions (lane 2). This indicated that the purified protein is, in fact, P6. No degradation products were observed.

Example 5

Large Scale Purification of Lipidated rP6 Using Differential Deterrent Membrane Extraction The fermentation broth of *E. coli* cells expressing lipidated rP6 was adjusted to 10 mM EDTA and diluted to less than or equal to 10% wet weight cells/volume prior to homogenization. The cells were then lysed with a high-pressure microfluidizer and diafiltered at room temperature with a sequence of buffers using a cross-flow membrane filtration device. It was determined that the minimum membrane area to allow efficient mass transport of solubilized proteins through the membrane was approximately 0.002 $m^2$/g wet weight cells. The solubilized proteins of approximate size less than the 1000 kD molecular weight cut-off rating of the membrane passed through with the permeate, while larger molecules and unsolubilized proteins were retained. The sequence of diafiltration steps was as follows:

(1) The lysed fermentation broth was diafiltered with 10 mM Hepes/1 mM EDTA/pH 8.0 (lysis buffer) at a volume equal to three times the volume of the retentate to remove intracellular and extracellular contaminants through the permeate.

(2) The lysate was diafiltered three times with 10 mM Hepes/1 mM $MgCl_2$/0.2% Triton™ X-100 to solubilize and remove inner membrane proteins. The $Mg^{++}$ ions stabilized the outer membrane, therefore, the outer membrane proteins were not solubilized in the presence of Triton™ X-100.

(3) The lysate was diafiltered three times with 50 mM Tris™/5 mM EDTA/0.2% Zwittergent™ 3-14 to solubilize and remove outer membrane proteins (but not lipidated rP6). The EDTA serves to sequester the $Mg^{++}$ ions from step (2), as well as to prevent proteolysis.

(4) The lysate was diafiltered three times with 50 mM Tris™/5 mM EDTA/0.5 M NaCl/0.2% Zwittergent™ 3-14 to solubilize and remove additional proteins. NaCl was added to the buffer in this step to disrupt any ionic interactions between membrane proteins and membranes. This step was performed because lipidated rP6 is a PAL, and the salt serves to remove membrane-bound proteins (but not lipidated rP6) from the membrane/outer membrane protein complex. The diafiltration was continued with three retentate volumes of 50 mM Tris™/5 mM EDTA to reduce the Zwittergent™ concentration in the retentate.

(5) The lysate was diafiltered three times with 50 mM Tris™/5 mM EDTA/0.2% sarcosyl to remove additional membrane bound proteins (but not lipidated rP6) and then diafiltered three times with 50 mM Tris™/5 mM EDTA to reduce the sarcosyl concentration in the retentate.

(6) The lysate was diafiltered three times with 10 mM phosphate/0.2% Zwittergent™3-12 to remove additional membrane bound proteins (but not lipidated rP6), and then diafiltered three times with 10 mM sodium phosphate to reduce the Zwittergent™ 3-12 concentration in the retentate.

(7) The lysate was concentrated to 20% of its original volume and then diafiltered three times with 10 mM sodium phosphate/0.2% Zwittergent™ 3-12 at 55° C. to solubilize lipidated rP6, which was collected through the permeate. The concentration step was performed prior to diafiltration to increase the concentration of lipidated rP6 in the permeate. The diafiltration was continued for three additional retentate volumes with 10 mM sodium phosphate at 55° C. to reduce the Zwittergent™ 3-12 concentration in the retentate. This heating step was performed because (as in step (4) above)) lipidated rP6 is a PAL, and heating serves to remove lipidated rP6 from the membrane/membrane protein complex. Finally, the diafiltration was concluded with three retentate volumes of 10 mM sodium phosphate at 55° C.

During the diafiltration steps, the transmembrane pressure was maintained at approximately 10 psi and the cross flow rate was maintained at approximately 120-180 lmh. All the diafiltration processes were run at room temperature, except the final 55° C. extraction step, which was run at the higher temperature to solubilize lipidated rP6. The permeate flux ranged from 30 to 50 lmh, which was sufficiently high for the extraction process to be practical and scalable.

During the extraction, samples were taken at various points for analysis by SDS-PAGE to evaluate the effect of various diafiltration steps on the extraction of proteins. Samples were precipitated by alcohol addition, centrifuged, and then resolubilized at 20% of the original volume in SDS sample prep buffer. This method of preparing samples concentrated the sample and reduced the Triton™ X-100 or Zwittergent™ 3-12 concentration of the samples. Triton™ X-100 or Zwittergent™ 3-12 interfere with the binding of SDS to the sample and reduced the resolution of bands on gels. Ten μl of each sample was loaded on to Novex 10% acrylamide gels and the gels were run for 60-90 minutes at 125 Volts.

Figure 3:
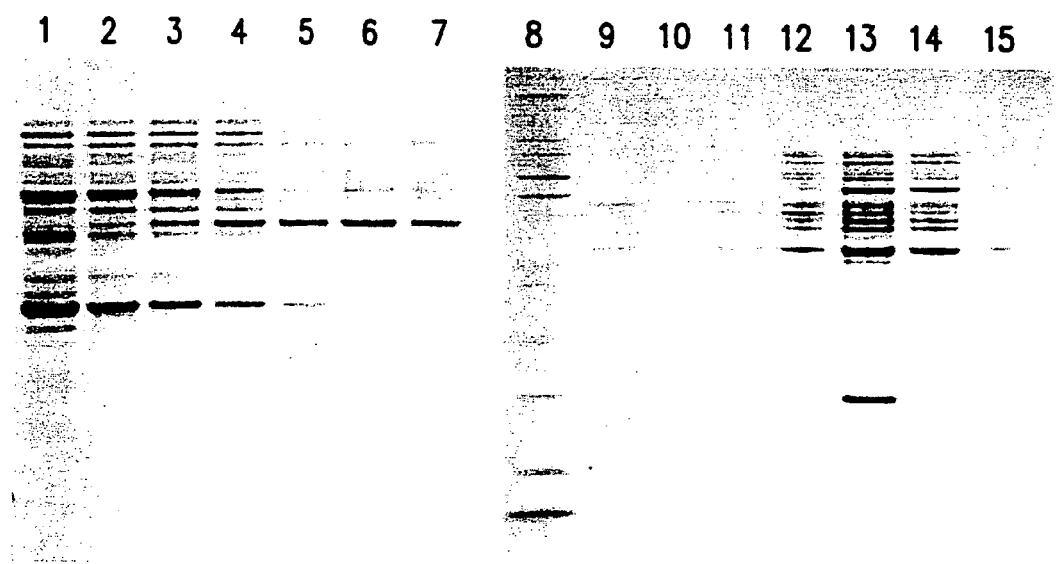
FIG. 3 depicts the SDS-PAGE analysis of fractions from the purification of lipidated rP6. Aliquots of steps in the purification process of lipidated rP6 were electrophoresed on a 4-20% gradient gel system. Lanes: 1, Permeate from diafiltration with lysis buffer; 2, Permeate from diafiltration with Triton™ X-100; 3, Permeate from diafiltration with Tris™ buffer; 4, Permeate from diafiltration with Zwittergent™ 3-14; 5, Permeate from diafiltration with Zwittergent™ 3-14/ 0.5 M NaCl; 6, Permeate from diafiltration with Tris™ buffer; 7, Permeate from diafiltration with sarcosyl; 8, Mark 12 Standard; 9, Permeate from diafiltration with Tris™ buffer; 10, Permeate from diafiltration with Zwittergent™ 3-12 at room temperature; 11, Permeate from diafiltration with Tris™ buffer; 12, Permeate from concentration step; 13, Permeate from diafiltration with Zwittergent™ 3-12 at 55° C.; 14, Permeate from diafiltration with Tris™ buffer at 55° C.; 15, Permeate from diafiltration with Zwittergent™ 3-12 at 55° C.

A typical SDS-PAGE analysis of the samples taken from the permeate streams during the extraction process of lipidated rP6 is shown in FIGS. 2 and 3. Lipidated rP6 ran at 15 kilodaltons (kD) on these gels. The gels show that some contaminating proteins were removed during diafiltration with lysis buffer and buffer containing various detergents. There was very little loss of lipidated rP6 during these diafiltration steps. During the final Zwittergent™ 3-12 diafiltration step at 55° C., lipidated rP6 was extracted in a partially purified state. At the end of the second Zwittergent™ 3-12 diafiltration step at 55° C., very little lipidated rP6 was present in the permeate stream. This suggested that most of the solubilized lipidated rP6 had been recovered through the permeate. Other experiments have shown that very little lipidated rP6 remained unsolubilized in the retentate after the completion of the diafiltration process. The 15 kD band of the Zwittergent™ 3-12/55° C. extract was shown to be lipidated rP6 by western analysis (data not shown).

The use of Zwittergent™ 3-12 in the solubilization of lipidated rP6 resulted in an extract that contained several proteins in addition to lipidated rP6. The homogeneity of this extract was determined to be approximately 78% lipidated rP6 (FIG. 2, Panel A, lane 1). While this is a high degree of homogeneity for an initial solubilization, it was desired to separate the LrP6 from these *E. coli* proteins if possible. This was carried out as described in Example 6.

Example 6

Further Purification of Purified Lipidated rP6 by Anion Exchange Chromatography Anion exchange chromatography was used to further purify the lipidated rP6 described in Example 5, because it has been used successfully to purify the non-lipidated rP6. The lipidated rP6 adsorbs more tightly to the DEAE resin than the rP6, which typically elutes with 0.1M NaCl. The lipidated rP6 in 0.2% Zwittergent™ required 0.2M NaCl in the buffer before desorbtion occurred. The *E. coli* proteins remained adsorbed to the anion exchange resin (DEAE) until after the lipidated rP6 was eluted.

The homogeneity and identity of the lipidated rP6 extracted and purified with 0.2% Zwittergent™ 3-12 are shown in FIG. 2. The homogeneity of the purified lipidated rP6 was determined to be greater than 98% (FIG. 2, Panel A, lane 2).

Example 7

Determination of Molecular Weight by MALDI-TOF Mass Spectral Analysis

Accurate measurement of the molecular weight of lipidated rP6 expressed from pPX4020 with the arabinose inducible promoter was carried out by Matrix Assisted Laser Desorption/Ionization Time-of-flight (MALDI-TOF) mass spectrometry using a Finnigan Mat Lasermat™ 2000 linear mass analyzer (Finnigan Mat, Ltd., San Jose, Calif.). The Lasermat™ uses the technique of matrix-assisted laser desorption (54) to ionize the sample and Time of Flight to analyze the ions produced. The sample was embedded in a matrix of 3,5-dimethoxy-4-hydroxy-cinnamic acid (sinapinic acid) to enhance ionization of the sample. One microliter of the sample containing 5-10 pmol of the purified protein was mixed with 1 μl of the matrix (10 mg/ml) dissolved in 70% (v/v) aqueous acetonitrile containing 0.1% (v/v) trifluoroacetic acid. One microliter of this sample and matrix mixture was loaded on a sample slide, allowed to dry and irradiated by a short pulse of UV light from a laser. Protein samples usually generate a relatively simple spectra in this method, since protein-related ions produced are predominantly of charge states $z=+1$ $[M+H]^+$ and $z=+2$ $[M+2H]^{2+}$. Cytochrome C from bovine heart (Sigma Chemical Co., St. Louis, Mo.) of molecular weight 12,230.9 was used for external calibration.

The molecular weight of lipidated rP6 in the sample used was determined to be 15,078. In addition to the expected $[M+H]^+$ molecular ion, the $[M+2H]^{2+}$ molecular ion of lipidated rP6 was also observed. The theoretical molecular weight of P6 containing a tripalmitoyl cysteine residue at its N-terminus is 15,024 and the predicted molecular weight of P6 unprocessed by signal peptidase II is 16,016.66, whereas the predicted molecular weight of unlipidated P6 cleaved by signal peptidase II is 14,234.66. Thus, these results are consistent with the expression of the lipidated form of rP6 by *E. coli*.

Example 8

Amino Acid Composition Analysis

A sample of lipidated rP6 for amino acid analysis was dried down in glass tubes, followed by hydrolysis using 100 μl of 6 N HCl containing 5% phenol and 1% 2-mercaptoethanol under vacuum for 22 hours at 110° C. The samples were subsequently dried under vacuum, followed by resolubilization in the sample dilution buffer Na-S (Beckman Instruments, Inc., Fullerton, Calif.). The amino acid composition was determined on a Beckman model 6300 Amino Acid Analyzer (55) using a three step Na-citrate gradient according to manufacturer's instructions. Threonine and serine residues were not corrected for destruction. Since cysteine and tryptophan residues were not determined by the method used, the results were expressed as mol of residues per mol of lipidated rP6 based on the theoretical molecular weight of unlipidated rP6 minus cysteines, which equals 14,132.4 (lipidated rP6 does not contain Trp). The results are shown in Table 1 and represent the mean of duplicate determinations. The results are consistent with the signal sequence of the pal gene having been removed by *E. coli*.

TABLE 1

Amino Acid Analysis of lipidated rP6

| Amino acid | Experimental mol residues/mol | Theoretical Mature mol residues/mol | Theoretical Pro-peptide mol residues/mol |
|---|---|---|---|
| Asp + Asn | 16.6 | 17 | 18 |
| Thr | 6.6 | 7 | 7 |
| Ser | 7.0 | 6 | 8 |
| Glu + Gln | 12.5 | 12 | 12 |
| Pro | 2.8 | 3 | 3 |
| Gly | 16.9 | 16 | 17 |
| Ala | 18.9 | 21 | 26 |
| Val | 10.5 | 10 | 13 |
| Met | 0.2 | 0 | 1 |
| Ile | 2.9 | 3 | 3 |
| Leu | 8.4 | 9 | 12 |
| Tyr | 10.1 | 11 | 11 |
| Phe | 3.1 | 3 | 4 |
| His | 3.1 | 2 | 2 |

TABLE 1-continued

Amino Acid Analysis of lipidated rP6

| Amino acid | Experimental mol residues/mol | Theoretical Mature mol residues/mol | Theoretical Pro-peptide mol residues/mol |
|---|---|---|---|
| Lys | 6.6 | 7 | 9 |
| Arg | 6.5 | 6 | 6 |
| Cys | ND | 1 | 1 |
| Trp | ND | 0 | 0 |

ND = Not determined

Example 9

Amino-Terminal Amino Acid Sequence Analysis

Amino-terminal protein sequence analysis was carried out using an Applied Biosystems Model 477A Protein/Peptide Sequencer equipped with an on-line Model 120A PTH Analyzer (Applied Biosystems, Foster City, Calif.). After the cleavage of each successive amino-terminus, the anilinothiazolinone derivative formed was converted to the more stable phenylthiohydantion (PTH) derivative by treatment with 25% trifluoroacetic acid at 64° C. for 20 minutes. The PTH derivatives were separated and identified on the PTH analyzer by reversed-phase HPLC using an Brownlee PTH C-18 column (particle size 5 μm, 2.1 mm i.d.×22 cm 1.; Applied Biosystems) with a modified two solvent gradient system developed by the manufacturer (56).

When lipidated rP6 (400 pmoles) was subjected to amino-terminal amino acid sequence analysis, no sequence data could be obtained. This suggested that the primary (or a secondary) amino group of the amino-terminal amino acid was not available for the sequencing chemistry, i.e., the amino-terminal residue of LrP6 was blocked. In order to substantiate that the inability to generate sequence data was not due to any instrument malfunction, a control experiment was subsequently run in which a mixture of 400 pmoles of lipidated rP6 and 200 pmoles of beta-lactoglobulin was subjected to amino-terminal sequence analysis. A single sequence representing the amino-terminal sequence of beta-lactoglobulin was obtained, which confirmed that the amino-terminal residue of lipidated rP6 was essentially blocked.

Example 10

Immunogenicity of Lipidated rP6 Compared to Non-lipidated rP6

The relative immunogenicity of the purified lipidated recombinant P6 and non-lipidated recombinant P6 (28) were compared in Swiss-Webster mice. Each five μg dose of each protein was mixed with 100 μg AlPO$_4$ and 50 μg 3-O-deacylated monophosphoryl lipid A (MPL™) (Ribi Immunochemicals, Hamilton, Mont.) were used to immunize mice subcutaneously at weeks 0, 4, and 6. Blood samples were taken at weeks 0, 4, 6, and 8. Other groups of mice were immunized with mixtures of either non-lipidated rP6 or lipidated rP6 and the UspA2 protein of Moraxella catarrhalis (49), a causative agent of bacterial otitis media, and recombinant lipidated rP4 (50). These mixtures were also adjuvanted with AlPO$_4$ and MPL™ as above.

Antisera obtained from the mice were analyzed by ELISA for antibodies against either the P6, P4, or UspA2 proteins. ELISA titers were determined (22, 28) for either pooled sera or individual animals and then the geometric mean titer (GMT) derived. The results are shown in Tables 2 and 3.

TABLE 2

Anti-P6 ELISA Titers

| Immunogen | | Week 0 | Week 6 | Week 8 |
|---|---|---|---|---|
| 5 μg rP6 (non-lipidated), | GMT | | 1,369 | 17,686 |
| | Pool | <50 | 40,715 | 147,985 |
| 5 μg rP6 (lipidated) | GMT | | 341,987 | 780,179 |
| | Pool | <50 | 706,826 | 786,917 |
| 5 μg each rP6 (non-lipidated), rP4, UspA | GMT | | 425 | 15,015 |
| | Pool | <50 | 692 | 64,913 |
| 5 μg each rP6 (lipidated), rP4, UspA | GMT | | 251,731 | 1,052,527 |
| | Pool | <50 | 739,896 | 1,268,527 |

TABLE 3

Anti-P4 and UspA2 ELISA Titers

| | | Anti-P4 ELISA Titer: | | Anti-UspA2 ELISA Titer: | |
|---|---|---|---|---|---|
| Immunogen | | Week 0 | Week 4 | Week 0 | Week 4 |
| 5 μg each rP6 (non-lipidated), rP4, UspA | GMT | | 84,677 | | 143,285 |
| | Pool | <50 | 189,980 | <50 | 247,003 |
| 5 μg each rP6 (lipidated), rP4, UspA | GMT | | 136,412 | | 257,751 |
| | Pool | <50 | 197,361 | <50 | 335,548 |

The lipidated rP6 is at least one log more immunogenic than the non-lipidated rP6 when administered alone with MPL™ and AlPO$_4$ adjuvants. When combined with rP4 and UspA2, no antigenic competition was observed. In fact, the response to the lipidated rP6 was increased to approximately 1.5 logo greater than the response to the non-lipidated rP6.

Anaylsis of the immune response to the UspA2 and rP4 antigens shows that the addition of the lipidated rP6 did not alter the immune response to these antigens as compared to addition of the non-lipidated rP6. Neither antigen had any effect on the normal immune response seen when lipidated rP4 and UspA2 were mixed together. This demonstrated the compatability of these antigens.

Example 11

Bactericidal Activity of Mouse Antisera

Biologic activity of the antisera directed against the lipidated rP6 and the lipidated rP6/rP4 mixtures was demonstrated using an in vitro bactericidal assay. This assay was performed as previously described (22, 28) using nontypable H. influenzae strain P861454 as the target. The results are shown in Table 4:

TABLE 4

In Vitro Bactericidal Activity Of Antisera From Tables 2 and 3

| | Week 6 Sera | | Week 8 Sera | |
|---|---|---|---|---|
| Immunogen: | BC Titer | Times (X) Background | BC Titer | Times (X) Background |
| rP6 | 3,200 | 8X | 12,800 | 16X |
| L-rP6 | 3,200 | 4X | 12,800 | 16X |

TABLE 4-continued

| | In Vitro Bactericidal Activity Of Antisera From Tables 2 and 3 | | | |
|---|---|---|---|---|
| | Week 6 Sera | | Week 8 Sera | |
| Immunogen: | BC Titer | Times (X) Background | BC Titer | Times (X) Background |
| rP6, rP4, UspA2 | 3,200 | 4X | 6,400 | 8X |
| L-rP6, rP4, UspA2 | 3,200 | 4X | 12,800 | 16X |

The results demonstrated that the lipidated rP6 elicited biologically active antibodies in this assay. While the absolute titers did not differ between the lipidated and non-lipidated antisera, this may be due to the antisera being maximally bactericidal in this assay system, especially since the preimmune sera demonstrated a high degree of nonspecific killing with the complement source used in this assay. The lipidated rP6/rP4 mixture also elicited bactericidal antibodies at titers equivalent to those obtained with the non-lipidated rP6/rP4 mixture. It was not possible to distinguish between the bactericidal activity of the anti-rP4 antibodies and the anti-rP6 antibodies in this assay, but it is clear that the mixture of the Haemophilus antigens elicited highly bactericidal antisera against nontypable H. influenzae.

BIBLIOGRAPHY

1. Ludwig, B., et al., *Infect. Immun.*, 59, 2515-2521 (1991).
2. Lazzaroni, J. C., et al., *Mol. Microbiol.*, 6, 735-742 (1992).
3. Spinola, S. M., et al., *Infect. Immun.*, 64, 1950-1955 (1996).
4. Burnens, A., et al., *J. Clin. Microbiol.*, 33, 2826-2832 (1995).
5. Rodriguez-Herva, J. J., et al., *J. Bacteriol.*, 178, 1699-1706 (1996).
6. Tibor, A., et al., *Infect. Immun.*, 62, 3633-3639 (1994).
7. Mizuno, T., *J. Biochem.* (Tokyo), 89, 1039-1049 (1981).
8. Frey, J., et al., *Res. Microbiol.*, 147, 351-361 (1996).
9. Tomb, J. F., et al., *Nature*, 388, 539-547 (Aug. 7, 1997).
10. PCT International Application Number WO 99/27105.
11. PCT International Application Number WO 99/28475.
12. Fraser, D. W., et al., *Am. J. Epidemiol.*, 100, 29-34 (1974).
13. Murphy, T. F., et al., *J. Infect. Dis.*, 152, 1300-1307 (1985).
14. Bluestone, C. D., and Klein, J. O., Pediatric Otolaryngology., p. 356 (Bluestone and Stool, eds., W.B. Saunders Co. Philadelphia (1983).
15. Musher, D. M., et al., *Ann. Intern. Med.*, 99, 344-350 (1983).
16. Walker, R. J., Jr., et al., *Ann. Rev. Infect. Dis.*, 5, 123-135 (1983).
17. Cherry J. D., and Dudley, J. P., Textbook of Pediatric Infectious Diseases, pages 103-105 (Feigin and Cherry eds., (W.B. Saunders & Co., Philadelphia, Pa. (1981)).
18. Munson, R., Jr., and Tolan, R. W., Jr., *Infect. Immun.*, 57, 88-94 (1989).
19. van Alphen, L., et al., *Infect. Immun.*, 59, 247-252 (1991).
20. Bernstein, J. M., et al., *Otolaryngol. Head Neck Surg.*, 105, 406-410 (1991).
21. U.S. Pat. No. 5,110,908.
22. Green, B. A., et al., *Infect. Immun.*, 59, 3191-3198 (1991).
23. Green, B. A., et al., *Infect. Immun.*, 55, 2878-2883 (1987).
24. Munson, R. S., Jr., and Granoff, D. M., *Infect. Immun.*, 49, 544-549 (1985).
25. Murphy, T. F., et al., *J. Clin. Invest.*, 78, 1020-1027 (1986).
26. Murphy, T. F., et al., *Infect. Immun.*, 54, 774-777 (1986).
27. Murphy, T. F., et al., *Pediatr. Infect. Dis. J.*, 8, S66-68 (1989).
28. Green, B. A., et al., *Infect. Immun.*, 58, 3272-3278 (1990).
29. Yang, Y. P., et al., *Vaccine*, 15, 976-987 (1997).
30. Green, B. A., and Deich, R. A, *Current Opinion in Therapeutic Patents*, 1, 669-680 (1991).
31. Green, B. A., et al., *Infect. Immun.*, 61, 1950-1957 (1993).
32. Akkoyunlu, M., et al., *Infect Immun.*, 65, 5010-5016 (1997).
33. Zlotnick, G. W., et al., *J. Biol. Chem.*, 263, 9790-9794 (1988).
34. Faden, H., et al., *J. Infect. Dis.*, 160, 999-1004 (1989).
35. Faden, H. S., et al., "Antibody response to nontypable *Haemophilus influenzae*." in Proceedings of the Fourth International Symposium on Otitis Media with Effusion., p. 340-343. (Lim, Bluestone, Klein and Nelson, eds. Toronto, Ontario, Canada (1987)).
36. Kodama, H., et al., *Acta Oto Laryngologica Supplement*, 523, 153-4 (1996).
37. Lim, A., Jr., et al., *Microbiology*, 143, 1709-1716 (1997).
38. Guzman, L.-M., et al., *J. Bacteriol.*, 177, 4121-4130 (1995).
39. Mertens, N., et al., *Gene*, 16, 9-15 (1995).
40. Mertens, N., *Biotechnology* (N.Y.), 13, 175-179 (1995).
41. Chandrashekharan, S., et al., *Biol. Chem.*, 379, 579-582 (1998).
42. Reddy, P., et al., *Nucleic Acids Res.*, 25, 10473-10488 (1989).
43. Sagawa, H., et al., *Gene*, 168, 37-41 (1996).
44. Waleh, N. S., *Gene*, 117, 7-14 (1992).
45. Skerra, A., *Gene*, 151, 131-5 (1994).
46. Haldimann, A., et al., *J. Bacteriol.*, 180, 1277-1286 (1998).
47. Lutz, R., et al., *Nucleic Acids Res.*, 25, 1203-1210 (1997).
48. Wulfing, C., *Gene*, 136, 199-203 (1993).
49. PCT International Application Number WO 98/28333.
50. U.S. Pat. No. 5,601,831.
51. PCT International Application Number WO 00/18434.
52. Sambrook, J., et al., *Molecular Cloning: A Laboratory Manual*, 2nd ed., Cold Spring Harbor Laboratory Press, Cold Spring Harbor, N.Y. (1989).
53. Laemmli, U.K., *Nature (London)*, 227, 680-685 (1970).
54. Hillenkamp, F., and Karas, M., *Meth. Enzymol.*, 193, 280-95 (1990).
55. Arrizon-Lopez, V., et al., "High-Performance Liquid Chromatography of Peptides and Proteins: Separation, Analysis, and Conformation." In p. 859-863. Hodges ed. (CRC Press. Boca Raton, Fla. 1991).
56. Sengoku, Y., et al., "Protein Analysis Renaissance" (Applied Biosystems. Foster City, Calif. 1993).

What is claimed is:

1. A plasmid containing a tightly regulated promoter, wherein said promoter is operatively linked to an isolated and purified DNA sequence that encodes a peptidoglycan-associated lipoprotein (recombinant PAL) of gram-negative bacteria, wherein the promoter is an arabinose inducible promoter.

2. The plasmid of claim 1 wherein the PAL is the P6 protein of *Haemophilus influenzae* (*H. influenzae*).

3. The plasmid of claim 1 wherein the plasmid is designated pPX4020.

4. A bacterial host cell transformed, transduced or transfected with the plasmid of claim 1.

5. A plasmid containing a T7 promoter, wherein said T7 promoter is operatively linked to an isolated and purified DNA sequence that encodes the P6 protein of *H. influenzae* (recombinant P6), wherein the recombinant P6 is under the control of only the T7 promoter.

6. The plasmid of claim 5 wherein the plasmid is designated pPX4019.

7. A bacterial host cell transformed, transduced or transfected with the plasmid of claim 5.

8. The bacterial host cell of claim 4, wherein the PAL is a lipidated recombinant P6 protein.

* * * * *